US008066989B2

(12) United States Patent
Lindhofer et al.

(10) Patent No.: US 8,066,989 B2
(45) Date of Patent: Nov. 29, 2011

(54) METHOD OF TREATING TUMOR GROWTH AND METASTASIS BY USING TRIFUNCTIONAL ANTIBODIES TO REDUCE THE RISK FOR GVHD IN ALLOGENEIC ANTITUMOR CELL THERAPY

(75) Inventors: Horst Lindhofer, Grobenzell (DE); Shimon Slavin, Jerusalem (IL); Shoshana Morecki, Jerusalem (IL)

(73) Assignee: Trion Pharma GmbH, Munich (DE)

( * ) Notice: Subject to any disclaimer, the term of this patent is extended or adjusted under 35 U.S.C. 154(b) by 361 days.

(21) Appl. No.: 11/000,484

(22) Filed: Nov. 30, 2004

(65) Prior Publication Data

US 2006/0115481 A1    Jun. 1, 2006

(51) Int. Cl.
    *A01N 63/00*    (2006.01)
    *A01N 65/00*    (2006.01)
    *A61K 39/395*   (2006.01)
    *A61K 39/00*    (2006.01)

(52) U.S. Cl. .................. 424/93.71; 424/93.1; 424/93.7; 424/133.1; 424/136.1

(58) Field of Classification Search .................. None
See application file for complete search history.

(56) References Cited

U.S. PATENT DOCUMENTS

| 5,985,276 | A | 11/1999 | Lindhofer et al. | |
| 6,210,668 | B1 | 4/2001 | Lindhofer et al. | |
| 6,551,592 | B2 * | 4/2003 | Lindhofer et al. | 424/136.1 |
| 6,994,853 | B1 * | 2/2006 | Lindhofer et al. | 424/136.1 |
| 7,018,632 | B2 | 3/2006 | Lindhofer et al. | |
| 2002/0009430 | A1 | 1/2002 | Lindhofer et al. | |
| 2002/0051780 | A1 | 5/2002 | Lindhofer | |
| 2003/0223999 | A1 * | 12/2003 | Lindhofer | 424/155.1 |
| 2005/0255110 | A1 | 11/2005 | Lindhofer et al. | |

FOREIGN PATENT DOCUMENTS

| EP | 0885614 | 12/1998 |
| WO | WO03/015705 | 2/2003 |

OTHER PUBLICATIONS

Ezzell, C. Cancer "Vaccines": an idea whose time has come? Journal of NIH Research, 1995. vol. 7, pp. 46-49.*
Forni, G., Lollini, P.L., Musiani, P., and Colombo, M.P. Immunoprevention of cancer: is the time ripe? Cancer Research, 2000. vol. 60, pp. 2571-2575.*
Ruf, P. and Lindhofer, H. Induction of a long-lasting antitumor immunity by a trifunctional bispecific antibody. Blood, 2001. vol. 98 No. 8, pp. 2526-2534.*
Slavin, S., Morecki, S., Weiss, L., and Or, R. Immunotherapy of hematologic malignancies and metastatic solid tumors in experimental animals and man. 2003. Critical Reviews in Oncology/Hematology. vol. 46, pp. 139-163.*
Kroesen, Haar, Spakman, Willemse, Sleijfer, De Vries, Mulder, Berendsen, Limburg, The, and De Leij. Local antitumor treatment in carcinoma patients with bispecific-monoclonal-antibody-redirected T cells. Cancer Immunology and Immunotherapy, 1993. vol. 37, pp. 400-407.*
European Search Report for corresponding European patent application No. 04028473.9 dated Jun. 28, 2005.
Simoes et al. "Bi20 a new trifunctional bispecific antibody (CD20XCD3) in the treatment of restraint B cell tumors: First Clinical data." *Blood*, 102 (11): p. 297b, Nov. 16, 2003. Abstract.
Simoes et al. "T cell response against CD20+ tumor cell lines and B-CLL cells induced by a new trifunctional bispecific antibody Bi20 (CD20XCD3)", *Blood*, 102 (11): p. 297b, Nov. 16, 2003. Abstract.
Sen et al. "Use of Anti-CD3 * Anti-HER2/neu Bispecific Antibody for Redirecting Cytotoxicity of Activated T Cells Toward HER2/neu+ Tumors", *Journal of Hematotherapy & Stem Cell Research*, 10: 247-260, 2001.
Slavin, Shimon, "Immunotherapy of Cancer with Alloreactive Lymphocytes" *The Lancet Oncology*, 2: pp. 491-498, 2001.
Childs et al., "Regression of Metastatic Reenal-Cell Carcinoma After Nonmyeloablative Allogeneic Peripheral-Blood Stem-Cell Transplantation" *Massachusetts Medical Society*, 343 (11): 754-758, Sep. 14, 2000.
European Search Report for corresponding European patent application No. 04028473.9 dated Sep. 29, 2005.
Schmitt et al., "Opsonization with a trifunctional bispecific (αCD3xαEpCAM) antibody results in efficient lysis in vitro and in vivo of EpCAM positive tumor cells by cytotoxic T lymphocytes", *International Journal of Oncology*, 25(4): pp. 841-848, Oct. 2004.
Fowler et al., "Clinical "Cytokine Storm" as Revealed by Monocyte Intracellular Flow Cytometry: Correlation of Tumor Necrosis Factor α With Severe Gut Graft-Versus-Host Disease", *Clinical Gastroenterology and Hepatology*, 2(3): pp. 237-245, Mar. 2004.
Zeidler et al., "The FC-Region of a new class of intact bispecific antibody mediates activation of accessory cells and NK cells and induces direct phagocytosis of tumour cells", *British Journal of Cancer*, 83(2): pp. 261-266, Jul. 2000.
Crespo et al., "Immunophenotypic and Functional Characterizations of Cord Blood Dendritic Cells", *Stem Cells and Development*, 13(1): pp. 63-70, Feb. 2004.
Verdonck et al., "Graft-versus-myeloma effect in two cases", *The Lancet*, 347(9004): pp. 800-801, 1996.

(Continued)

*Primary Examiner* — Anne M. Gussow
(74) *Attorney, Agent, or Firm* — Jenkins, Wilson, Taylor & Hunt, P.A.

(57) ABSTRACT

The present invention refers to a method of treating tumor growth and metastasis in a mammal, the treating comprising administering allogeneic effector cells together with trifunctional bispecific or trispecific antibodies or a combination thereof having the following properties:

a) binding to a T cell b) binding to at least one antigen on a tumor cell c) binding via their Fc portion in the case of trifunctional bispecific antibodies or via third specificity in the case of trispecific antibodies to Fc receptor positive cells;

the antibodies redirecting the allogenic cells away from host tissues in order to substantially reduce or avoid a graft versus host disease.

15 Claims, 2 Drawing Sheets

OTHER PUBLICATIONS

Simoes et al., "T Cell Response Against B Cell Tumor Lines Induced by Bi20, a Novel Trifunctional Bispecific (CD20×CD3) Anitbody", *Blood, W.B. Saunders Company*, 100(11): Abstract No. 4789, Nov. 16, 2002.

Lindhofer et al. Bispecific antibodies effectively purge cancer cells from peripheral blood stem cells collections without affecting colony forming units. Experimental Hematology, vol. 25, (1997), pp. 879.

Communication Pursuant to Article 94(3) EPC corresponding to European Application No. 04 028 473.9-2401 dated Jul. 2, 2009.

Harris, D., "In vitro and in vivo assessment of the graft-versus-leukemia activity of cord blood," Bone Marrow Transplantation, vol. 15, pp. 17-23 (1995).

Haagen et al., "Interaction of human monocyte Fc gamma receptors with rat IgG2b," J. Immunology, vol. 154, pp. 1852-1860 (1995).

Lindhofer et al., "Preferential species-restricted heavy/light chain pairing in rat/mouse quadromas. Implications for a single-step purification of bispecific antibodies," J. Immunol., vol. 155, pp. 219-225 (1995).

Mocikat et al., "A Mouse Model for the Preclinical Evaluation of Immunosuppressive Effector Functions of Human Isotypes: The Human IgG1 Isotype is Superior to IgG3," Transplantation 57 (1994), 405.

Abramowicz et al., "Release of Tumor Necrosis Factor, Interleukin-2, and Gamma-Interferon in Serum After Injection of OKT3 Monoclonal Antibody in Kidney Transplant Recipients," Transplantation, vol. 47, No. 4, pp. 606-608 (Apr. 1989).

Baeuerle et al., "Bispecific antibodies for polyclonal T-cell engagement," Curr. Opin. Mol. Ther., vol. 5, No. 4, pp. 413-419 (2003).

Canevari et al., "Regression of advanced ovarian carcinoma by intraperitoneal treatment with autologous T lymphocytes retargeted by a bispecific monoclonal antibody," J. Natl. Cancer Inst., vol. 87, pp. 1463-1469 (1995).

Cohen et al., "Spontaneous and IL-2 induced anti-leukemic and anti-host effects against tumor- and host-specific alloantigens," J. Immunol., vol. 151, pp. 4803-4810 (1993).

De Gast et al., "CD8 T cell activation after intravenous administration of CD3×CD19 bispecific antibody in patients with non-Hodgkin lymphomas," Cancer Immunol. Immunother., vol. 40, pp. 390-396 (1995).

Dreier et al., "Extremely potent, rapid and costimulation-independent cytotoxic T cell response against lymphoma cells catalayzd by a single-chain bispeicifc antibody," Int. J. Cancer, vol. 100, pp. 690-697 (2002).

Friedrich et al., "Antibody-directed effector cell therapy of tumors: analysis and optimization using a physiologically based pharmacokinetic model," Neoplasia, vol. 4, No. 5, pp. 449-463 2002).

Gratwohl, "Graft-versus-host disease and outcome in HLA-identical sibling transplantations for chronic myeloid leukemia," Blood, vol. 100, No. 12, pp. 3877-3886 (Dec. 1, 2002).

Kolb et al., "Graft-versus-leukemia effect of donor lymphocyte transfusions in marrow grafted patients: European Group for Blood and Marrow Transplantation Working Party Chronic Leukemia," Blood, vol. 86, pp. 2041-2050 (1995).

Kolb et al., "Graft-versus-leukemia reactions in allogeneic chimeras," Blood, vol. 103, No. 3, pp. 767-776 (Feb. 1, 2004).

Kudo et al., "Specific targeting immmunotherapy of cancer with bispecific antibodies," Tohoku J. Exp. Med., vol. 188, No. 4, pp. 275-288 (1999).

Lindhofer et al., "Bispecific antibodies effectively purge cancer cells from peripheral blood stem cells collections without affecting colony forming units," Experimental Hematology, vol. 25, pp. 879 (1997).

Marme et al., "Intraperitoneal bispecific antibody (HEA 125×OKT3) therapy inhibits malignant ascites production in advanced ovarian carcinoma," Int. J. Cancer, vol. 101, pp. 183-189 (2002).

Morecki et al., "Allogeneic cell therapy for a murine mammary carcinoma," Cancer Res., vol. 58, pp. 3891-3895 (1998).

Morecki et al., "Cell therapy with preimmunized effector cells mismatched for minor histocompatible antigens in the treatment of a murine mammary carcinoma," J. Immunother., vol. 24, No. 2, pp. 114-121 (2001).

Perez et al., "Specific targeting of cytotoxic T cells by anti-T3 linked to anti-target cell antibody," Nature, vol. 316, pp. 354-356 (1985).

Renner et al., "The role of lymphocyte subsets and adhesion molecules in T cell dependent cytotoxicity mediated by CD3 and CD28 bispecific monoclonal antibodies," Eur. J. Immunol., vol. 25, pp. 2027-2033 (1995).

Riesenberg et al., "Lysis of prostate carcinoma cells by trifunctional bispecific antibodies (alpha EpCAM×alpha CD3)," J. Histochem Cytochem., vol. 49, No. 7, pp. 911-917 (2001).

Segal et al., "Alternative triggering molecules and single chain bispecific antibodies," J. Hematother., vol. 4, No. 5, pp. 377-382 (1995).

Shalaby et al., "Development of Humanized Bispicitic Antibodies Reactive with Cytotoxic Lymphocytes and Tumor Cells Overexpressing the HER2 Protooncogene," J. Exp. Med., vol. 175, pp. 217-225 (1992).

Slavin et al., "Allogeneic cell therapy for relapsed leukemia after bone marrow transplantation with donor peripheral blood lymphocytes," Exp. Hematol., vol. 23, No. 14, pp. 1553-1562 (Dec. 1995).

Slavin et al., "Allogeneic cell therapy with donor peripheral blood cells and recombinant human interleukin-2 to treat leukemia relapse post allogeneic bone marrow transplantation," Blood, vol. 87, No. 6, pp. 2195-2204 (1996).

Slavin S., "Cancer Immunotherapy with alloreactive lymphocytes," N. Engl. J. Med., vol. 343, pp. 802-803 (2000).

Sullivan et al., "Influence of acute and chronic graft-versus-host disease on relapse and survival after bone marrow transplantation from HLA-identical siblings as treatment of acute and chronic leukemia," Blood, vol. 73, No. 6, pp. 1720-1728 (1989).

Went et al., "Frequent EpCam protein expression in human carcinomas," Human Pathology, vol. 35, Issue 1, pp. 122-128 (Jan. 2004). Abstract.

Wimberger et al., "Efficient tumor cell lysis by autologous, tumor-resident T lymphocytes in primary ovarian cancer samples by an EP-CAM-/CD3-bispecific antibody," Int. J. Cancer, vol. 105, No. 2, pp. 241-248 (Jun. 10, 2003).

* cited by examiner

METHOD OF TREATING TUMOR GROWTH AND METASTASIS BY USING TRIFUNCTIONAL ANTIBODIES TO REDUCE THE RISK FOR GVHD IN ALLOGENEIC ANTITUMOR CELL THERAPY

TECHNICAL FIELD

The present invention relates to a method of treating tumor growth and metastasis in a mammal, preferably a human and particularly to a method of reducing the risk for acute, chronic or lethal GvHD and to improve the GVT effects during allogeneic antitumor cell therapy.

BACKGROUND ART

Therapeutic options for patients with recurrent leukemia or B cell lymphoma refractory to the standard therapy are limited. A promising approach for such resistant malignancies is immunotherapy with e.g. donor lymphocyte infusions (1-3). Donor lymphocyte infusions can cure especially recurrent chronic myelogenous leukemia, probably by the action of T cells, but is complicated by the possibility of simultaneously induced graft-versus-host disease. Therefore, a more specific and better controllable therapy, e.g. with monoclonal antibodies that target lymphocytes to residual tumor cells, is desired. However, in most cases, unlabeled or unconjugated antibodies do not activate immune effector mechanisms sufficiently to eradicate all tumor cells. Thus, T cell redirecting bispecific antibodies (bsAb), which combine the cell-specificity of monospecific antibodies with the potency of T cells may be more effective.

Bispecific antibodies consisting of 2 different antigenic specificities have been developed as immunotherapeutic reagents for targeting immune cells to tumor tissue (4-8). This strategy is based on the assumption that appropriate effector/target cell interaction via a physical contact between immune cells and tumor cells, activates cytotoxic mechanisms that lead to an efficient eradication of tumor cells.

Many different bispecific antibody formats have been created over the last 20 years with varying qualities in production, in vitro and in vivo efficacy, recruitment of effector cells or e.g. need for additional T cell stimuli (9-13). Finally, several of these constructs reached the clinic with minor to moderate and only sometimes promising efficacy (14-17). Trifunctional antibodies (trAb) are artificially engineered immunoglobulins with an unique composition of heavy chains of mouse IgG2a and rat IgG2b, representing highly homologous Ig subclasses. Both isotypes are very potent in terms of immunological effector functions, such as complement dependent cytotoxicity (CDC) and antibody dependent cell-mediated cytotoxicity (ADCC). Noteworthy, the Fc region composed by these two subclasses, effectively binds to human FcγI and III-receptors on accessory cells (like e.g. macrophages, dendritic cells and natural killer cells) but not to the inhibitory Fcγ receptor type II expressed e.g. on B cells. As a consequence trAbs can not only redirect T-cells to tumor cells, but also induce recruitment and activation of accessory cells through their Fc region. The simultaneous activation of different mechanisms at the tumor site such as phagocytosis, perforin mediated lysis and cytokine release results in a particularly efficient destruction of tumor cells (18, 19). Remarkably, also apoptosis-resistant tumor cells can be eliminated by this process (19). As a further consequence of the so induced uptake of tumor material by the antigen presenting system even a long-lasting protective antitumor immunity could be established as already demonstrated in two immunocompetent murine tumor models (20).

While most BsAb treatments aiming to achieve anti-tumor response have been combined with syngeneic/autologous derived cells, we and others (3, 10, 21-23) have also used an immunotherapeutic strategy based on the allogeneic reaction of major histocompatibly mismatched cells, known in clinical practice as donor lymphocyte infusion (DLI), following hematopoietic stem cell transplantation (SCT). Unfortunately, the use of allogeneic cell therapy (alloCT) in the context of currently applicable protocols in experimental models and in clinical practice, is frequently accompanied by life-threatening acute and chronic graft versus host disease (GVHD) that is difficult to control effectively with currently available treatments (23-28).

SUMMARY OF THE INVENTION

It is therefore an object of the present invention to provide a new therapeutic method for treating tumor growth and metastasis in a mammal, preferably a human, wherein life-threatening acute and chronic graft versus host disease (GVHD) is either efficiently reduced to a level not threatening the patient's life or is even avoided.

This object is achieved by providing a method of treating tumor growth and metastasis in a mammal, preferably a human, said method comprising administering allogeneic effector cells together with trifunctional antibodies having the following properties:
a) binding to a T cell
b) binding to at least one antigen on a tumor cell
c) binding via their Fc portion in the case of trifunctional bispecific antibodies or via a third specificity in the case of trispecific antibodies to Fc receptor positive cells, said antibodies redirecting the allogeneic cells away from host tissues in order to substantially reduce or avoid a graft versus host disease.

It is a further object of the present invention to provide a new therapeutic composition for treating tumor growth and metastasis in a mammal, preferably a human, wherein life-threatening acute and chronic graft versus host disease (GVHD) is either efficiently reduced to a level not threatening the patient's life or is even avoided.

This object is achieved by providing a pharmaceutical composition for treating tumor growth and metastasis in a mammal, said composition comprising a therapeutically effective amount of allogeneic effector cells together with trifunctional antibodies having the following properties:
a) binding to a T cell
b) binding to at least one antigen on a tumor cell
c) binding via their Fc portion in the case of trifunctional bispecific antibodies or via a third specificity in the case of trispecific antibodies to Fc receptor positive cells together with pharmaceutically acceptable carriers and auxiliary substances.

Preferred embodiments are further described in the following description, the experimental section in combination with the figures and the enclosed claims.

It has surprisingly been found that a combination of trifunctional bispecific antibodies (trAbs) and/or trispecific antibodies, as defined herein, with allogeneic effector cells (said method called allogeneic cell therapy=alloCT) allows to direct alloreactive effector cells to tumor tissue rather than to normal host cells, thereby allowing development of more efficient graft-versus-tumor (GVT) effect as well as to minimize the risk of GVHD. In the here presented rationale, a therapy is designed to treat recipients with cancer cells, expressing tumor-associated antigens (e.g. EpCAM, Her2/neu or CD20) as the targeting molecule, with trifunctional bispecific antibodies and/or trispecific antibodies, given together with allogeneic effector cells, particularly donor lymphocytes and/or myeloid cells, in order to assess their capability to selectively eliminate tumor cells while sparing normal host cells in an attempt to avoid lethal GVHD.

BRIEF DESCRIPTION OF THE FIGURES

The invention will be illustrated in more detail by means of the accompanying Figures. The Figures show.

BALB/c×C57BL/6)F$_1$ mice were inoculated intraperitoneally (IP) with $5×10^4$ B16-EpCAM melanoma cells 24 h after conditioning with TBI 4Gy. One day later, $30×10^6$ naïave or rIL-2 activated C57BL/6 splenocytes were administered IP with or without pretreatment with BiLu antibodies (10 µg/mouse).

Figure 2:
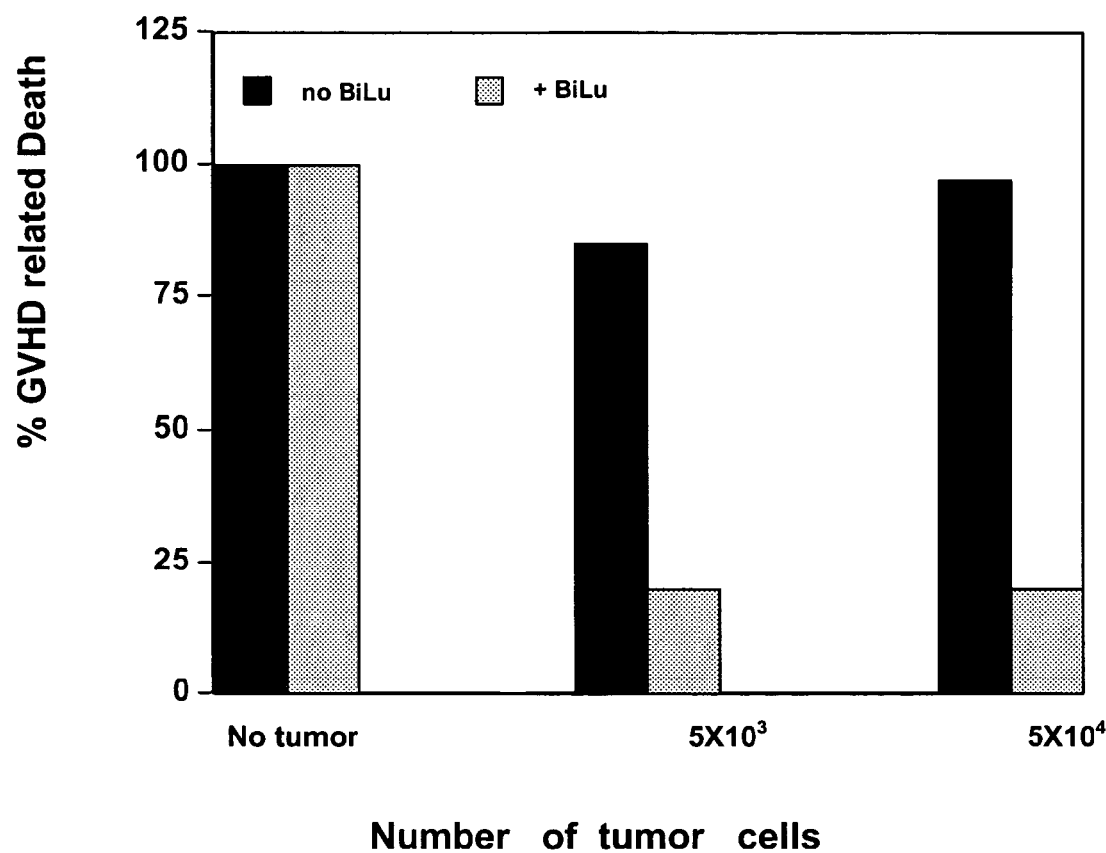

FIG. 2. The role of tumor burden on susceptibility to GVHD induced by alloreactive spleen cells with or without pretreatment with BiLu.

Sublethally irradiated (BALB/c×C57BL/6)F$_1$ mice were conditioned with TBI 4Gy. One day following TBI, mice were injected IP with $5×10^3$ or $5×10^4$ B16-EpCAM melanoma cells or left without tumor inoculation. One day later, mice were inoculated intraperitoneally (IP) with $30×10^6$ naïve C57BL/6 splenocytes with or without pretreatment with BiLu (10 µg/mouse) in order to determine the possible role of tumor existence on targeting of alloreactive lymphocytes, guided by BiLu, to the tumor for desirable prevention of GVHD while attempting to maximize GVT effects.

DESCRIPTION OF THE PREFERRED EMBODIMENTS

The trifunctional antibodies to be used in the present invention are known in the art and are described in several documents. Reference is made e.g. to U.S. Pat. No. 6,551,592, US2003223999, US2002051780, and U.S. Pat. No. 6,210,668 and the articles indicated above; all of these documents and the following references are fully incorporated by reference into this application.

The antibodies to be used in the present invention are preferably characterized by the additional effects of
   activation of the Fc receptor-positive cell by binding to the Fc receptor-positive cell via Fcγ receptors of type I and III (CD64 and CD16) (18) and, thereby, initiating or increasing the expression of cytokines and/or costimulatory antigens; and
   transfer of at least a second activation signal, required for physiological activation of the T cell, to the T cell by the co-stimulatory antigens and/or cytokines, this activation being indicated by up-regulation of activation markers, killing of the tumor cell, and/or T cell proliferation.

Preferably, the antibodies used in the method and composition of the present invention are also able to activate tumor-specific T cells recognizing a tumor-specific peptide presented on the tumor cells by MHC class I and/or class II via their T cell receptor upon binding to the trifunctional bispecific or trispecific antibody as described herein.

Further, the antibodies used according to the invention are preferably able to reactivate the tumor-specific T cells being in an anergic state. Furthermore, they are preferably able to induce tumor-reactive complement-binding antibodies and, thus, induce a humoral immune reaction.

Binding to the T cell takes place via CD3, CD2, CD5, CD28, and/or CD44. The Fc receptor-positive cells have at least one Fcγ receptor I or III.

The antibody used according to the invention is able to bind to monocytes, macrophages, and/or dendritic cells being Fcγ receptor I-positive cells.

The antibodies used according to the invention lead to the initiation or increase of the expression of CD40, CD80, CD86, ICAM-1, and/or LFA-3 being co-stimulatory antigens and/or secretion of cytokines by the Fc receptor-positive cell. Preferably, the cytokines are IL-1, IL-2, IL-4, IL-6, IL-7, IL-8, IL-12, INF-gamma and/or TNF-[alpha].

Preferably, binding to the T cell takes place via the T cell receptor complex of the T-cell.

The trifunctional bispecific antibody used in the invention preferably is an anti-CD3 X anti-tumor-associated antigen antibody and/or anti-CD2 X anti-tumor-associated antigen antibody and/or anti-CD5 X anti-tumor-associated antigen antibody and/or anti-CD28 X anti-tumor-associated antigen antibody and/or anti-CD44 X anti-tumor-associated antigen antibody.

The trispecific antibody used according to the invention preferably is an anti-CD3 X anti-tumor-associated antigen antibody and/or anti-CD2 X anti-tumor-associated antigen antibody and/or anti-CD5 X anti-tumor-associated antigen antibody and/or anti-CD28 X anti-tumor-associated antigen antibody and/or anti-CD44 X anti-tumor-associated antigen antibody having an additional anti-Fc receptor binding arm.

Regarding feature (a), the first signal is for example transduced via the T cell receptor complex of the T cell and, therefore, may itself lead to an unphysiological T cell activation. By this, the cell could be anergized and unable to react to T cell receptor-mediated stimuli. In addition, a second activation signal is transduced to the T cell by the trifunctional bispecific or trispecific antibodies of the invention via the co-stimulatory antigens on the simultaneously bound Fc receptor-positive cell which causes physiological activation of the T cell and, subsequently, leads to killing of the tumor cell and/or proliferation of the T cell. As a further criterion for T cell activation the up-regulation of cell surface antigens such as CD2, CD25, and/or CD28, and/or the secretion of cytokines such as e.g. IL-2 or INF-gamma may be used.

Thus, by the use of the trAbs described according to the invention T cells and accessory cells are activated and retargeted simultaneously against the tumor cells.

Preferred antibodies are heterologous trifunctional bispecific antibodies selected of one or more of the following combinations of isotypes:
   rat-IgG2b/mouse-IgG2a,
   rat-IgG2b/mouse-IgG2b,
   rat-IgG2b/mouse-IgG3;
   rat-IgG2b/human-IgG1,
   rat-IgG2b/human-IgG2
   rat-IgG2b/human-IgG3 [oriental allotype G3m(st)=binding to protein A], rat-IgG2b/human-IgG4;
   rat-IgG2b/rat-IgG2c;
   mouse-IgG2a/human-IgG3 [caucasian allotypes G3m(b+g)=no binding to protein A, in the following indicated as *]
   mouse-IgG2a/mouse-[VH-CH1, VL-CL]-human-IgG1-[hinge]-human-IgG3*-[CH2-CH3]
   mouse-IgG2a/rat-[VH-CH1, VL-CL]-human-IgG1-[hinge]-human-IgG3 *-[CH2-CH3]
   mouse-IgG2a/human-[VH-CH1, VL-CL]-human-IgG1-[hinge]-human-IgG3*-[CH2-CH3]

mouse-[VH-CH1, VL-CL]-human-IgG1/rat-[VH-CH1, VL-CL]-human-IgG1-[hinge]-human-IgG3*-[CH2-CH3]
mouse-[VH-CH1, VL-CL]-human-IgG4/rat-[VH-CH1, VL-CL]-human-IgG4-[hinge]-human-IgG4 [N-terminal region of CH2]-human-IgG3*[C-terminal region of CH2:>aa position 251]-human-IgG3*[CH3]
at-IgG2b/mouse-[VH-CH1, VL-CL]-human-IgG1-[hinge-CH2-CH3]
rat-IgG2b/mouse-[VH-CH1, VL-CL]-human-IgG2-[hinge-CH2-CH3]
rat-IgG2b/mouse-[VH-CH1, VL-CL]-human-IgG3-[hinge-CH2-CH3, oriental allotype]
rat-IgG2b/mouse-[VH-CH1, VL-CL]-human-IgG4-[hinge-CH2-CH3]
human-IgG1/human-[VH-CH1, VL-CL]-human-IgG1-[hinge]-human-IgG3*-[CH2-CH3]
human-IgG1/rat-[VH-CH1, VL-CL]-human-IgG1-[hinge]-human-IgG4 [N-terminal region of CH2]-human-IgG3*[C-terminal region of CH2:>aa position 251]-human-IgG3*[CH3]
human-IgG1/mouse-[VH-CH1, VL-CL]-human-IgG1-[hinge]-human-IgG4 [N-terminal region of CH2]-human-IgG3*[C-terminal region of CH2:>aa position 251]-human-IgG3*[CH3]
humaterminal n-IgG1/rat-[VH-CH1, VL-CL]-human-IgG1-[hinge]-human-IgG2 [N-terminal region of CH2]-human-IgG3*[C-terminal region of CH2:>aa position 251]-human-IgG3*[CH3]
human-IgG1/mouse-[VH-CH1, VL-CL]-human-IgG1-[hinge]-human-IgG2 [N-terminal region of CH2]-human-IgG3*[C-terminal region of CH2:>aa position 251]-human-IgG3*[CH3]
human-IgG1/rat-[VH-CH1, VL-CL]-human-IgG1-[hinge]-human-IgG3*-[CH2-CH3]
human-IgG1/mouse-[VH-CH1, VL-CL]-human-IgG1-[hinge]-human-IgG3*-[CH2-CH3]
human-IgG2/human-[VH-CH1, VL-CL]-human-IgG2-[hinge]-human-IgG3*-[CH2-CH3]
human-IgG4/human-[VH-CH1, VL-CL]-human-IgG4-[hinge]-human-IgG3*-[CH2-CH3]
human-IgG4/human-[VH-CH1, VL-CL]-human-IgG4-[hinge]-human-IgG4 [N-terminal region of CH2]-human-IgG3*[C-terminal region of CH2:>aa position 251]-human-IgG3*[CH3]
mouse-IgG2b/rat-[VH-CH1, VL-CL]-human-IgG1-[hinge]-human-IgG3 *-[CH2-CH3]
mouse-IgG2b/human-[VH-CH1, VL-CL]-human-IgG1-[hinge]-human-IgG3*-[CH2-CH3]
mouse-IgG2b/mouse-[VH-CH1, VL-CL]-human-IgG1-[hinge]-human-IgG3*-[CH2-CH3]

The trifunctional bispecific and trispecific antibodies described in the method of the present invention are characterized in particular by the features described in the claims and preferably of course by the features (a)-(c) described in claim 1. Thus, these antibodies may be used together with allogeneic effector cells in humans and animals in a pharmaceutical preparation, e.g. in donor lymphocyte infusions.

Preferably, specific subclasses or combinations of subclasses, respectively, of the trAb or in the case of trispecific antibodies a binding arm recognizing the Fc receptor are employed for the activation of the Fc receptor-positive cell. For example, in vitro experiments showed that intact bsAb of the mouse-IgG2a/rat-IgG2b subclass combination are able to bind to and simultaneously activate Fc receptor-positive cells leading to up-regulation or new formation (expression), respectively, of co-stimulatory antigens such as e.g. CD40, CD80, or CD86 on the surface of these cells, whereas bsAb of the mouse-IgG1/rat-IgG2b subclass combination are able to bind to Fc receptor-positive cells (Haagen et al., Interaction of human monocyte Fc[gamma] receptors with rat IgG2b, J. Immunology, 1995, 154:1852-1860) but obviously are unable to activate these cells to a comparable extent (Gast G. C., Haagen I.-A., van Houten A. A., Klein S., Duits A. J., de Weger R. A., Vroom T. M., Clark M. R., J. Phillips, van Dijk A. J. G., de Lau W. B. M., Bast B. J. E. G. CD8 T-cell activation after intravenous administration of CD3*CD19 bispecific antibody in patients with non-Hodgkin lymphoma. Cancer Immunol. Immunother. 40:390, 1995).

While the intact bsAb binds to the T cell with one binding arm (e.g. CD3 or CD2) and activates it at the same time, co-stimulatory signals from the Fc receptor-positive cell bound to the Fc portion of the bsAb can be transferred to the T cell. That means, only the combination of T cell activation via one binding arm of the bsAb and simultaneous mediation of co-stimulatory signals from the Fc receptor-positive cell to the T cell leads to efficient T cell activation.

Also tumor-specific T cells which have been insufficiently activated at the tumor cell site and, therefore, remain in an anergic state may be reactivated.

A physiological activation of tumor-retargeted T cells is achieved by 1) binding of the bsAb to the T cell, for example via the T cell receptor complex, and 2) simultaneous transfer of co-stimulatory signals by FcR+ cells binding to the Fc portion of the bsAb.

Thus, an important prerequisite for an efficient reduction of GVHD is the use of trAbs having a Fc portion able to bind to FcγR+ cells which are activated themselves by this event and, thereby, able to mediate co-stimulatory signals to the T cell in combination with the redirection of effector cells away from healthy host tissue towards tumor cells.

Due to this mechanism, tumor-specific anergic T cells (having a T cell receptor [TCR] which recognize tumor-specific peptides in association with MHC molecules on the tumor cell) can be reactivated at the tumor cell site, and thereby tumor tolerance can be reversed.

Since the tumor-specific T cells via their TCR are able to recognize completely different peptides/proteins than the trAb via its anti-tumor binding arm, additional tumor cells may be recognized and killed after activation of such T cells by the trAb. That means, it is not neccessary for the trAb to recognize all of the tumor cells which in a second step subsequently can be eliminated by activated T cells with an adequate T cell receptor.

Preferably, the antibodies according to the invention are monoclonal, chimeric, recombinant, synthetic, semi-synthetic, or chemically modified intact antibodies having for example Fv, Fab, scFv, or F (ab)2 fragments.

In the method of the present invention also antibodies or derivatives or fragments of human origin can be used, or antibodies modified to be suitable for the use in humans (so-called "humanized antibodies") (see for example Shalaby et al., J. Exp. Med. 175 (1992), 217; Mocikat et al., Transplantation 57 (1994), 405).

The preparation of the different types of antibodies and antibody fragments mentioned above is obvious to the skilled artisan. The preparation of monoclonal antibodies preferably of mammalian origin, e.g. of human, rat, mouse, rabbit, or goat, can be performed using conventional methods for example as those described in Köhler and Milstein (Nature 256 (1975), 495), in Harlow and Lane (Antibodies, A Laboratory Manual (1988), Cold Spring Harbor) or in Galfre (Meth. Enzymol. 73 (1981), 3).

It is further possible to prepare the antibodies described by means of recombinant DNA technology according to techniques obvious to the skilled artisan (see Kurucz et al., J. Immunol. 154 (1995), 4576; Hollinger et al., Proc. Natl. Acad. Sci. USA 90 (1993), 6444).

The preparation of antibodies having two different specificities, the so-called bispecific antibodies, can be performed for example using recombinant DNA technology but also by the so-called hybrid hybridoma fusion technique (see for example Milstein et al., Nature 305 (1983), 537). This technique consists of fusing hybridoma cell lines each producing antibodies having one of the desired specificities and identifying and isolating recombinant cell lines producing antibodies having both specificities.

The problem forming the basis of the invention can be overcome using either trifunctional bispecific or trispecific trifunctional antibodies if they exhibit the properties and effects as described herein. The invention is particularly described by the way of trifunctional bispecific antibodies. However, it is understood that it also covers the following trispecific antibodies exhibiting similar effects.

The preparation of antibodies exhibiting three specificities, so-called trispecific antibodies, also suitable to solve the basic problem of the invention may for example be carried out by coupling a third antigen binding site having an additional specificity, e.g. in the form of "single chain variable fragments" (scFv) to one of the IgG heavy chains of a bispecific antibody. The scFv may be coupled for example using a-S-S (G4S)nD-I(SEQ ID NO:1)linker to one of the heavy chains (S=serine, G=glycine, D=aspartate, I=isoleucine).

Analogously, trispecific F(ab)2 constructs may be prepared by replacing the CH2-CH3 regions of the heavy chain of one specificity of a bispecific antibody by an scFv having a third specificity, while the CH2-CH3 regions of the heavy chain having the other specificity can be removed for example by insertion of a stop codon (at the end of the "hinge" 5 region) into the coding gene, e.g by homologous recombination.

It is also possible to prepare trispecific scFv constructs wherein three VH-VL regions representing three different specificities are arranged in series.

According to the invention there are intact bispecific antibodies used. Intact bispecific antibodies are composed of two antibody semi-molecules (each having a H and a L immunoglobulin chain) each representing a specificity, and additionally like normal antibodies having a Fc portion performing the well-known effector functions. They are preferably prepared using the quadroma technology. This method of preparation is exemplified in DE-A-44 19 399. For complete disclosure this document is incorporated in its entirety by reference also with respect to a definition of bispecific antibodies. It should be understood that other methods of preparation are also useful if they lead to the intact bispecific antibodies according to the above definition required according to the invention.

For example, intact bispecific antibodies may be produced in sufficient amounts using a newly developed method of preparation (Lindhofer et al., J. Immunology, 155:219 (1995)). The combination of two bispecific antibodies directed against two different tumor-associated antigens (e.g. c-erb-B2, EpCAM, such as GA-733-2=C215) on the mammary carcinoma cells minimizes the risk that tumor cells expressing only one of the antigens remain unidentified.

Bispecific antibodies are able to bind to the T cell receptor complex on the T cell with one binding arm and to tumor-associated antigens on the tumor cell with the second binding arm. Thereby, T cells are activated which kill the tumor cells by releasing cytokines or by apoptosis-mediating mechanisms. In addition, there is the possibility that T cells recognize tumor-specific antigens by their receptor during activation by the bispecific antibodies and, thereby, a long-lasting immunization is initiated. Of particular importance in this respect is the intact Fc portion of the bispecific antibody which mediates the binding to accessory cells such as monocytes/macrophages/dendritic cells and causes these cells to develop cytotoxicity, and/or concomitantly transfer important co-stimulatory signals to the T cell.

The antibodies according to the invention uses preferably intact bsAb able to bind to Fc[gamma]RI+ cells via their Fc portion. In addition, the bsAb used according to the invention have as a second specificity besides the tumor cell-binding specificity for example anti-CD3, i.e. they are able to bind to T cells via the second binding arm. Thus, by the bsAb used according to the invention T cells are activated and redirected against the tumor cells.

The present invention comprises two main embodiments:
1. In the first embodiment, the patient to be treated has undergone an allogeneic bone marrow transplantation or an allogeneic stem cell transplantation. After having been transplanted, the patient will be administered with the allogeneic effector cells together with the trifunctional bispecific and/or trispecific antibodies as indicated herein. Administration of the allogeneic effector cells is also referred to as donor lymphocyte infusion (DLI). DLI refers to a method of treating cancer in which effector cells of lymphoid and/or myeloid origin are transferred, particularly by infusion, into the person who received the original bone marrow or stem cell transplant.
2. In a second embodiment of the invention, allogeneic effector cells in combination with said trifunctional bispecific and/or trispecific antibodies can be administered in a pharmaceutical preparation by the way of allogeneic donor lymphocyte infusion into patients which received a mild immunosuppression or conditioning (by an e.g. sublethal radiation dose) without having received an allogeneic bone marrow or stem cell transplantation before. In this embodiment, the conditioning allows the infused allogeneic effector cells to survive for a time period which is necessary to accomplish tumor cell killing before rejection. That means that a host versus graft reaction will not immediately attack and destroy the effector cells of the DLI. Moreover, such a variation would further minimize the risks of an allogeneic bone marrow or stem cell transplantation which currently are limiting a broader application of this therapy.

DLI comprises the infusion of lymphocytes from a bone marrow donor into a person who received the original transplant. Donor lymphocyte infusion has mainly been used to treat relapsed chronic myelogenous leukemia (CML). Patients with relapsed acute leukemia, chronic lymphocytic leukemia (CLL), myelodysplasia (MDS), Hodgkin disease, non-Hodgkin lymphoma (NHL), and multiple myeloma have also been treated by DLI.

The allogeneic effector cells and the trifunctional bispecific antibodies and/or trispecific antibodies can be either administered to the patient in need thereof separately or preferably in admixture. In a preferred method of the invention, the effector cells and the antibodies are pre-incubated for a time period of up to two hours, preferably for a time between 5 minutes and 30 minutes, most preferably about 2 hours. Further preferred is a time limit of about 1 minute to 10 minutes.

A person skilled in the art, particularly a physician working in the field of immunology, will know about the conditions which are more preferably to be used and how to adapt them to a particular patient and disease. It is state of the art to make appropriate variations and adaptions to the present method in order to provide the best benefit for the patient to be treated.

The most characteristic feature of the malignant tumor treatment method and composition according to the invention is that a malignant tumor can be treated while preventing or avoiding or at least sufficiently reducing the onset of GVHD as an adverse effect, which is one of the most important drawbacks of the technique of DLI.

The malignant tumor which can be treated by the method of this invention includes malignant tumors of hematopoietic cells, such as leukemia, malignant lymphoma, and multiple myeloma; malignant tumors other than those of the hematopoietic cells, for example melanoma, sarcoma, and brain tumor; and all organ cancers (solid cancers) such as stomach cancer, tongue cancer, esophageal carcinoma, colorectal cancer, liver cancer, gallbladder carcinoma, pancreatic carcinoma, renal carcinoma, bladder cancer, nasopharyngeal cancer, laryngeal cancer, skin cancer, mammary cancer, testicular cancer, ovarian cancer, uterus carcinoma, and lung cancer.

In the second method of the invention, DLI is first performed in a patient with malignant tumor to replace transiently the hematopoietic system of the patient with that of a donor. The thus-constructed donor-derived hematopoietic system (mainly T lymphocytes) attacks the tumor cells of the patient in the manner of GVT, damaging and killing them and producing a curative effect on the tumor. On the other hand, the donor-derived hematopoietic system regards normal tissues of the patient as a foreign matter and causes GVHD to eliminate the same. In accordance with the invention, however, together with allogeneic effector cells contained in DLI the trifunctional antibodies of the present invention as defined above are infused in a patient in need thereof whereby the onset of GVHD can be prevented or at least substantially reduced.

The method and composition of the invention make it possible to inhibit or avoid or effectively lower GVHD as an adverse effect possibly induced by DLI and cure various sorts of malignant tumor by preferably repeating DLI several times in combination with trifunctional antibodies by which in order to erase malignant tumor growth and reoccurrence.

The DLI employed in accordance with the invention can be performed basically in the same manner as the conventional DLI in recurrence therapy for leukemic cells (cf. Shintaro Shiobara, Hematology & Oncology, 42(2):151-157, 2001).

The donor is preferably a normal or related subject. Further, the donor is allogeneic to the patient (host), to whom the method of the invention is to be applied. The histocompatibility antigens (HLA) of the donor can be matched or mismatched in several loci compared to the recipient.

The donor lymphocytes to be used in DLI are included in cell collections (preparations) selected from peripheral blood mononuclear cells (PBMCs), whole bone marrow cells, splenic cells or other sources as e.g. cord blood derived from the allogeneic donors mentioned above. The collection and preparation of PBMCs can be performed e.g. by apheresis or bone marrow puncture.

The allogeneic effector cells used in the DLI and contained in the apheresate are mainly of lymphoid and myeloid origin comprising accessory cells as e.g. monocytes, macrophages, dendritic cells and natural killer cells. These effector cells express Fcγ receptors of type I, II and III. Moreover, all types of T cells can be present.

In the practice of the invention, DLI is carried out preferably in the manner of intravenous infusion of e.g. PBMCs. In particular, those PBMC preparations obtained by the ordinary method contain T cells at a level of about 20% or higher.

The amount of e.g. PBMCs to be transfused and the frequency of transfusions can be appropriately determined depending on the condition (age, sex, body weight) of the patient (host) and the severity of disease, among others, without any particular restriction. Generally, the amount is usually selected within the range of about 5×10e6 to 1×10e8 cells/kg per shot. The frequency of transfusions and the interval thereof may be such that the desired GVT-based curative effect on malignant tumor can be produced. Generally, at least two, usually about 3-5, transfusions are performed usually at intervals of 4-60 days.

For increasing the treatment efficiency of this DLI on malignant tumor, the method of the invention may further comprise subjecting the host to irradiation treatment as a pretreatment prior to DLI and antibody application. This irradiation treatment should destroy as much lymphatic system and hematopoietic cells of the host as necessary to mitigate or avoid host versus graft reaction. Generally, total body irradiation at a dose of at most about 4-5 Gy is sufficient. This total body irradiation is preferably performed on the same day (within 24 hours) as the day of DLI (first time).

The present invention also provides a pharmaceutical composition for performing the above-described method for the treatment of malignant tumor growth and metastasis. The composition comprises a composition containing donor-derived allogeneic effector cells and trifunctional antibodies as defined herein in a therapeutically effective amount, preferably in combination with pharmaceutically acceptable carries, diluents, auxiliary substances etc.

Generally, those compositions are prepared preferably in the form suited for the route of administration thereof, for example in the form of injections, transfusions or like liquids or solutions. The liquid or solution forms, inclusive of injections, can be prepared in the same manner as in preparing various conventional pharmaceutical preparations containing cell components of this kind. The carrier to be used on that occasion may be any of various pharmaceutically acceptable carriers (diluents) so far well known in this field of art. Specific examples thereof are physiological sodium chloride solution, PBS and RPMI 1640. In preparing the above-mentioned liquid or solution forms, various technologies currently in general use in preparing various transfusions can be used. The respective compositions may be prepared just prior to use. The respective compositions are administered at respective predetermined doses via a predetermined route(s) of administration according to the method of the invention.

The DLI employed in accordance with the invention can be performed basically in the same manner as the conventional DLI in recurrence therapy for leukemic cells (cf. Shintaro Shiobara, Hematology & Oncology, 42(2):151-157, 2001).

The problem of the present invention has been solved as demonstrated in the following experiments. The example is to be understood to exemplify the invention; the invention is however not restricted to this particular embodiment. A person skilled in the art will be able to make the necessary modifications and adaptations within the spirit of this invention.

EXAMPLE 1

Materials and Methods

Mice

Female BALB/c H-2d (BALB), C57BL/6 H-2b (C57) and (BALB×C57BL/6)F$_1$ H-2$^{d/b}$ (F$_1$) mice aged 10-12 weeks and weighing 22-24 grams, were used in this study. All mice were purchased from Harlan, Israel, and maintained in the animal facility of the Hadassah University Hospital with sterilized food and water ad libitum, in full compliance with the regulations for the protection of animal rights.

Tumor Cells

A murine model of melanoma cell line (B-16) transfected with human EpCAM was used in the experiments (7). The tumor cells were maintained in RPMI 1640 medium supplemented with 5% fetal bovine serum (FBS) (GIBCO, N.Y., USA), 2 mM L-glutamine, 1% non-essential amino acids, 1 mM sodium pyruvate, 0.5 mg/ml geneticin (GIBCO, N.Y., USA) 100 U/ml penicillin, and 100 μg/ml streptomycin. All culture supplements (except FBS and geneticin) were purchased from Biological Industries, Beit HaEmek, Israel. Cells were kept at 37° C. in a humidified 5% $CO_2$ air incubator. B-16-EpCAM cells were harvested by 0.25% trypsin in 0.05% EDTA, washed with RPMI 1640 and resuspended for intraperitoneal (IP) inoculation (0,25 ml/mouse).

Spleen Cells

Splenocytes were prepared by teasing spleen cells over a metal mesh, then filtering them through nylon mesh and suspending them in phosphate buffered saline (PBS) for IP injection ($30 \times 10^6$ /mouse).

Radiation Therapy

Sublethal total body irradiation (TBI) was administered using a 6MEV linear accelerator at a dose rate of 1.9 Gy/min (400 cGy) in order to prevent rejection of donor spleen cells used for induction of GVHD and graft-versus-tumor (GVT) effects.

Antibody Treatment

The trifunctional bispecific antibody (BiLu) consisting of specific antigen binding regions directed against murine CD3 and human EpCAM (20) was used in the experiments. BiLu was given intraperitoneal (IP) either alone or in conjunction with cell therapy (10 μg/mouse).

Experimental Design

Recipient $F_1$ mice were conditioned with non-lethal TBI of 4 Gy. Twenty-four hours later, $5 \times 10^3$ or $5 \times 10^4$ B-16-EpCAM tumor cells were inoculated IP. On the following day, $30 \times 10^6$ naïve spleen cells derived from C57 or BALB donors were incubated with BiLu antibodies for 10 min and then the mixture was inoculated IP.

Follow-Up

In all experiments, mice were checked daily for the appearance of signs and symptoms of GVHD such as hunched posture, ruffled fur, diarrhea and cachexia as assessed by weight. Body weight was measured on a weekly basis. Survival was monitored and GVHD-related death was determined if mice were showing GVHD symptoms as described above. In addition, mice were investigated post mortem for detection of the presence of tumor metastases in the peritoneum, in order to determine tumor- related death.

Flow Cytometry Analysis

B16-EpCAM tumor cells ($4 \times 10^5$) were incubated with 0.5 μg BiLu antibody in staining buffer (PBS containing 1% bovine serum albumin and 0.03% sodium azide) for 30 min. on ice, then washed and incubated with FITC F(ab')2 fragment mouse anti-rat IgG (H+L) (Jackson ImmunoResearch Laboratories, INC, Pa. USA) for 30 min on ice. Tumor cells were analyzed by FACS (FACStar™ Plus; Becton-Dickinson, Calif., USA) and the percentage of tumor cells expressing EpCAM determinant was measured. In all tests >88% B16-EpCAM cells stained positive (data not shown).

Statistical Analysis

Body weights were presented as mean±SE (standard error). The Kaplan-Meier method was used to calculate the probability of survival as a function of time after tumor inoculation. The statistical significance of survival between pairs of Kaplan-Meier curves was evaluated by the log rank test. Statistical significance of differences in body weights of control versus BiLu treated mice was evaluated by standard two-tailed, unpaired student t-test. A value of $p<0.05$ was considered statistically significant.

Results

The Effect of BiLu Treatment on GVHD Symptoms

Figure 1:
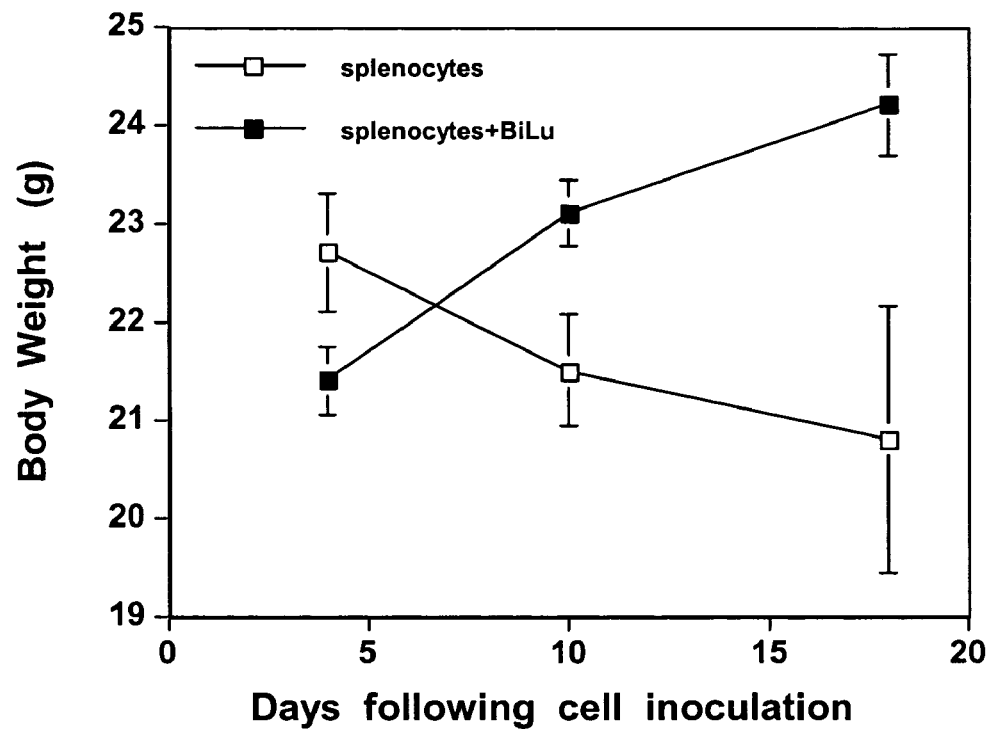
FIG. 1. The effect of allogeneic cell therapy with or without BiLu on development of GVHD assessed by measurement of body weight.

GVHD was induced by intravenous inoculation of naïve splenocytes derived from C57 donors in sublethally irradiated $F_1$ mice that had been inoculated with $5 \times 10^3$ B16-EpCAM tumor cells. A high percentage of mice inoculated with naïve C57 splenocytes (23/27) displayed GVHD symptoms such as hunched posture, ruffled fur, diarrhea and loss of 2 grams of body weight over 18 days (FIG. 1). On the other hand, only 5/25 mice inoculated with BiLu pretreated C57 splenocytes displayed GVHD symptoms. Most of the mice inoculated with C57 cells pretreated with BiLu, gained 2-3 grams in weight over 18 days (FIG. 1) and maintained a normal healthy appearance for >170 days. Differences in body weight of untreated as compared with BiLu pretreated naïve splenocytes obtained from C57 mice on days 10 and 18 was statistically significant ($p<0.05$).

One injection of naïve BALB splenocytes into $F_1$ mice inoculated with B16-EpCAM tumor cells, caused mild GVHD symptoms, such as hunched posture and ruffled fur; After a second administration of BALB splenocytes these symptoms were more prominent although there was no significant loss of body weight (data not shown) and most of the mice finally recovered. In contrast, mice inoculated with BALB splenocytes pretreated with BiLu antibodies, did not display any signs or symptoms of GVHD during a follow-up period of >250 days and also showed no signs of tumor growth.

The GVT effect of host allogeneic lymphocytes and trifunctional bispecific antibody C57 splenocytes, which are syngeneic to the B16-EpCAM tumor cells but haploidentically mismatched to the host cells, were inoculated into sublethally irradiated $F_1$ mice with or without BiLu pretreatment. Control $F_1$ mice injected with $5 \times 10^3$ cells tumor cells and inoculated with C57-derived naïve splenocytes, died of GVHD (23/27) after a median of 20 days, while GVHD-related death in $F_1$ mice treated with BiLu pretreated naïve C57 splenocytes was observed only in 5/25 (p=0.000). Sixteen out of 25 mice treated with BiLu pretreated naïve cells, remained tumor-free with no signs of GVHD for a median of >212 days (Table 1).

TABLE 1

Effect of trifunctional bispecific antibody (BiLu) on GVHD and GVT
induction by C57BL/6 spleen cells in mice inoculated with $5 \times 10^3$ B16 EpCAM
melanoma cells

| Effector cells (C57BL/6) | BiLU pretreatment (10 μg/ml) | Survival (days) Median (range) | Cause of Death Tumor | Cause of Death GVHD | Disease free survivors |
|---|---|---|---|---|---|
| – | – | 33 (24 –> 212) | 60 }p = 0.000 | – | 7 }p = 0.000 |
| – | + | >212 (24 –> 212) | 3 | – | 7 |
| Splenocytes | – | 20 (14 –> 212) | 3 }p = 0.005 | 23 }p = 0.000 | 1 }p = 0.000 |
| Splenocytes | + | >212 (25 –> 212) | 4 | 5 | 16 |

(BALB/c/cXC57BL/6)$F_1$ mice were inoculated with $5 \times 10^3$ B16-EpCAM melanoma cell 24 h after conditioning with sublethal TBI (4 Gy). One day later, $30 \times 10^6$ naïve C57BL/6 splenocytes were given intraperitoneally with or without pretreatment with BiLu (10 μg/mouse). p values are shown for the comparison of GVT and GVHD with or without BiLu pretreatment of C57BL/6 naïve cells.

BiLu treatment without cell therapy had an anti-tumor effect on mice inoculated with a low tumor cell dose of $5 \times 10^3$. Its efficacy in preventing GVHD, in tumor-bearing mice supposedly by targeting the donor T cells to the tumor, encouraged us to test its effect in mice inoculated with a higher tumor cell dose ($5 \times 10^4$), proved lethal in 100% of untreated mice (68/68) with a median survival of 21 days. Although BiLu treatment without cell therapy had also a substantial anti-tumor effect on the high tumor cell dose (10/17 mice remained tumor-free), BiLu treatment given concomitantly with allogeneic cell therapy using C57 naïve splenocytes, resulted in 10/20 healthy appearing mice with no GVHD and no evidence of tumor for >250 days. Treatment with BiLu, protected recipients of alloreactive C57 spleen cells as GVHD-related death was observed in only 4/20 mice inoculated with naïve C57 cells, whereas 31/32 untreated control mice inoculated with untreated naïve cells died of GVHD after a median of 19 days (Table 2).

(BALB/c/cXC57BL/6)$F_1$ mice were inoculated with $5 \times 10^4$ B16-EpCAM melanoma cell 24 h after conditioning with sublethal TBI (4 Gy). One day later, $30 \times 10^6$ naïve C57BL/6 splenocytes were given intraperitoneally with or without pretreatment with BiLu (10 μg/mouse). p values are shown for the comparison of GVT and GVHD with or without BiLu pretreatment of C57BL/6 naïve cells.

The Effect of BiLu Treatment on Allogeneic Cell Therapy

BALB splenocytes which are fully mismatched to B16-EpCAM tumor cells but haploidentically mismatched to host alloantigens, were inoculated into sub-lethally irradiated $F_1$ mice with or without prior pretreatment with BiLu. One dose of BALB splenocytes in mice inoculated with $5 \times 10^3$ tumor cells neither produced a graft versus tumor (GVT) effect (18/32 mice died of tumor) nor caused lethal GVHD (only 1/32 mice died of GVHD) (Table 3). Two doses of BALB splenocytes, however, induced GVT effect accompanied with severe GVHD, resulting in 6/27 tumor-related deaths, 7/27 GVHD related death and 14/27 disease free survivors. Mice inoculated with $5 \times 10^3$ tumor cells and treated with BiLu and one or two doses of BALB splenocytes, led to 19/20 and 10/10 tumor- and GVHD-free mice respectively, after a follow-up period of >212 days (Table 3).

TABLE 2

Effect of trifunctional bispecific antibody (BiLu) on GVHD and GVT
induction by C57BL/6 spleen cells in mice inoculated with $5 \times 10^4$ B16 EpCAM
melanoma cells

| Effector cells (C57BL/6) | BiLU pretreatment (10 μg/ml) | Survival (days) Median (range) | Cause of Death Tumor | Cause of Death GVHD | Disease free survivors |
|---|---|---|---|---|---|
| – | – | 21 (17-34) | 68 }p = 0.000 | – | 0 }p = 0.000 |
| – | + | >220 (30 –> 220) | 7 | – | 10 |
| Splenocytes | – | 19 (14 -39) | 1 }p = 0.006 | 31 }p = 0.000 | 0 }p = 0.000 |
| Splenocytes | + | >290 (26 –> 290) | 6 | 4 | 10 |

TABLE 3

Effect of trifunctional bispecific antibody (BiLu) on GVHD and GVT induction by BALB/c spleen cells in mice inoculated with $5 \times 10^3$ B16 EpCAM melanoma cells

| Effector cells (BALB/c) | BiLu pretreatment (10 μg/ml) | Survival (days) Median (range) | Cause of Death Tumor | Cause of Death GVHD | Disease free survivors |
|---|---|---|---|---|---|
| – | – | 33 (24-212) | 60 | – | 7 |
|   |   |   | }p = 0.000 |   | }p = 0.000 |
| – | + | >212 (24 -> 212) | 3 | – | 7 |
| ¹Splenocytes | – | 66 (26 -> 212) | 18 | 1 | 13 |
|   |   |   | }p = 0.000 | }p = 0.0244 | }p = 0.000 |
| Splenocytes | + | >212 (43 -> 212) | 1 | 0 | 19 |
| ²Splenocytes | – | >196 (170 -> 212) | 6 | 7 | 14 |
|   |   |   | }p = 0.109 | }p = 0.031 | }p = 0.007 |
| Splenocytes | + | >212 | 0 | 0 | 10 |

(BALB/c×C57BL/6)F₁ mice were inoculated with 5×10³ B16-EpCAM melanoma cell 24 h after conditioning with sublethal TBI (4 Gy). Naive 1⁽¹⁾ or 2⁽²⁾ doses BALB splenocytes (30×10⁶) were administered intraperitoneally with or without pretreatment with BiLu (10 μg/mouse) one day later. Cell therapy with 2 doses versus 1 dose of BALB splenocytes, both without BiLu, significantly (p=0.006) reduced number of tumor related death, significantly (p=0.039) increased number of GVHD related death, but was not statistically different for the disease free survivors (p=0.186).

TABLE 4

Effect of trifunctional bispecific antibody (BiLu) on GVT and GVHD in mice inoculated with $5 \times 10^4$ B16 EpCAM melanoma cells

| Effector cells (BALB/c) | BiLU pretreatment (10 μg/ml) | Survival (days) Median (range) | Cause of Death Tumor | Cause of Death GVHD | Disease free survivors |
|---|---|---|---|---|---|
| – | – | 21 (17-34) | 68 | – | 0 |
|   |   |   | }p = 0.000 |   | }p = 0.000 |
| – | + | >220 (30 -> 220) | 7 | – | 10 |
| Splenocytes | – | 52 (17 -> 245) | 26 | 0 | 6 |
|   |   |   | }p = 0.002 | }p = 0.541 | }p = 0.000 |
| Splenocytes | + | >286 (22 -> 286) | 8 | 1 | 13 |

(BALB/c×C57BL/6)F₁ mice were inoculated with 5×10⁴ B16-EpCAM melanoma cell 24 h after conditioning with sublethal TBI (4 Gy). One day or/and 5 days following tumor inoculation, 30×10⁶ BALB splenocytes were given intraperitoneally with or without pretreatment with BiLu (10 μg/mouse).

The effect of BiLu treatment on GVHD induction in tumor-free in comparison with mice inoculated with B 16-EpCAM tumor cells.

Since BiLu treatment was very efficient in preventing GVHD in tumor-bearing mice, it was interesting to test its effect on GVHD induction in tumor-free mice. Results presented in FIG. 2 show that injection of haploidentically mismatched C57 splenocytes into F₁ mice that had not been inoculated with tumor cells induced lethal GVHD in 18/18 animals. Pre-treatment of naïve C57 cells with BiLu did not prevent GVHD-related death in 5/5 mice. The median survival of these mice was 19 and 24 days respectively, in comparison with median survival of 76 and 30 days for 5/25 mice and for 4/20 mice inoculated with 5×10³ or 5×10⁴ tumor cells and treated with BiLu, respectively. Statistical analysis revealed that pretreatment of the GVHD inoculum with BiLu in mice inoculated with 5×10³ or 5×10⁴ tumor cells produced a significantly better anti-GVHD effect in comparison with similarly treated tumor-free recipients inoculated with BiLu pretreated C57 cells (p=0.000).

It could be shown by the experiments described above that trifunctional bispecific antibodies, BiLu, e.g. directed against human tumor antigen (EpCAM) and murine CD3, given with lymphocytes fully alloreactive against the host, successfully prevented lethal GVHD while exerting an efficient anti-tumor effect, leading to disease-free survival of >250 days in mice inoculated with EpCAM transduced B16 melanoma. The anti-GVHD effect of BiLu was especially evident in sublethally irradiated F₁ mice inoculated with parental C57 splenocytes. Since the intensity of GVHD induced by a similar dose of parental naïve BALB splenocytes was far less dramatic, as has already been discussed elsewhere, the anti-GVHD effect of BiLu in this setting could not be evaluated. However, when two doses of BALB derived splenocytes were given, and more severe GVHD developed, the anti-GVHD effect of BiLu was clearly evident.

Our main goal was to determine the possible role of tumor existence on targeting the alloreactive lymphocytes by BiLu to the tumor in order to achieve the most efficient GVT effect while controlling or minimizing GVHD development.

Remarkably, the anti-GVHD effect of BiLu was clearly depended on the presence of tumor cells bearing the EpCAM antigen in the recipient (FIG. 2). While even a low dose of tumor cells was sufficient to confer significant protection from lethal GVHD in 80% of the mice, BiLu did not prevent GVHD induction in naïve non-tumor bearing F₁ mice inoculated with C57 splenocytes (FIG. 2). It is reasonable to assume that in the absence of tumor, BiLu was ineffective in preventing the donor cells from targeting GVHD-sensitive organs in the host. In view of another report showing that in the absence of tumor target, BsAb treatment by itself does not activate systemic stimulation of T cells, one may assume that the GVHD that occurred in non-tumor bearing $F_1$ hosts was mediated primarily by the inoculated spleen cells themselves, without the risk of engagement of BiLu activated host cells.

As shown here and as reported previously (20), BiLu treatment alone given after inoculation of a low dose of tumor cells can provide an efficient anti-tumor effect.

The anti-tumor effect mediated by C57 splenocytes alone could not be evaluated due to the incidence of severe and lethal GVHD. In contrast, some beneficial GVT effect (13 of 32 mice survived, table 3) could be observed after treatment with naïve BALB splenocytes without additional BiLu, since GVHD was mild and non-lethal. This anti-tumor effect was further amplified (14 of 27 mice survived, table 3) by inoculation of 2 consecutive doses of BALB splenocytes (p<0.006) for comparison with one dose of BALB or, as a control, of tumor alone. The use of alloCT by itself has previously been shown to be an effective immunotherapeutic strategy for achieving GVL/GVT effects in experimental animal models of leukemia and mammary carcinoma, as well as in patients with hematological malignancies and metastatic solid tumors (26). However, GVT effects against tumor cells were dramatically improved by the addition of BiLU treatment (10 of 10 mice survived, table 3) which enhanced the targeting of alloreactive effector cells, while diverting such cells away from host tissues susceptible to GVHD. Remarkably, no mouse was lost due to GvHD in the BiLu group whereas 7 out of 27 mice died of GvHD and 6 of 27 due to tumor growth, after 2 splenocyte infusions in the non-BiLu group.

Due to the trifunctional properties of the BiLu (CD3× EpCAM) used in our study, it was feasible to target either naive splenocytes containing $CD3^+$ T cells or $Fc\gamma R^+$ NK cells, as well as monocytes and antigen-presenting dendritic cells, all of which may contribute to the achievement of a most effective anti-tumor response. Since in many primary tumor cells, and more frequently in metastatic cells, the expression of class I MHC antigens is either lost or suppressed, the combination of T cell dependent and the non-MHC-restricted killing activity exerted by accessory cells, may circumvent aberrant down-regulated MHC expression by tumor cells.

The BiLu antibodies directed to CD3 and EpCAM antigens serve as a relevant model for a variety of e.g. epithelial tumors over-expressing EpCAM or Her2/neu or other malignancies expressing further tumor-associated antigens as target antigens on their surface (13,15,17).

Although in principle, bispecific antibodies can be used alone, through activation of the patients own cells, the combination of such constructs with alloCT would make it possible to benefit from different anti-cancer effector mechanisms in order to achieve maximal targeting of anti-cancer effector cells to the tumor site, while in parallel, avoiding or minimizing the risk of uncontrolled GVHD.

Summarizing, bispecific monoclonal antibodies (BiLu) directed against murine CD3 and a tumor-associated antigen of human epithelial cell adhesion molecule (EpCAM) were tested for their ability to induce cell-mediated adoptive immunotherapy in a murine melanoma (B-16) model of C57BL/6 (C57) mice transfected with EpCAM. Naïve or rIL-2 activated splenocytes (LAK) induced lethal graft versus host disease (GVHD) in 64-97% of sub-lethally irradiated (BALB/c×C57BL/6)$F_1$ ($F_1$) hosts inoculated with a sub-lethal ($5\times10^3$) or lethal ($5\times10^4$) dose of tumor cells. BiLu antibodies given concomitantly with alloreactive C57 cells, effectively prevented GVHD-related-and tumor-related death in 16/25 and 8/12 mice inoculated with $5\times10^3$ tumor cells and treated with naïve or LAK C57 cells, respectively, as well as in 10/20 and 22/27 mice inoculated with $5\times10^4$ tumor cells treated with naïve or LAK C57 cells, respectively, over a follow-up period of >250 days. Naïve or LAK cells derived from BALB/c (BALB) mice caused mild GVHD which was lethal in only 0-27% of the $F_1$ mice, while they exerted an efficient graft versus tumor effect which was further improved by BiLu treatment given concomitantly with naïve but not with LAK BALB splenocytes, probably due to excessive activation of BALB against the fully MHC mismatched tumor cells. Bispecific antibodies capable of cross-linking T lymphocytes, natural killer, and other $Fc\gamma R^+$ effector cells to the tumor cells, may be applied together with adoptive allogeneic cell therapy to maximize anti-tumor responses while acting on GVHD in patients with minimal residual disease.

REFERENCES (1) Slavin S, Naparstek E, Nagler A, Ackerstein A, Kapelushnik J, Or R. Allogeneic cell therapy for relapsed leukemia after bone marrow transplantation with donor peripheral blood lymphocytes. Exp Hematol. 1995 December;23(14): 1553-62.

(2) Kolb H J, Schattenberg A, Goldman J M, et al. Graft-versus-leukemia effect of donor lymphocyte transfusions in marrow grafted patients: European Group for Blood and Marrow Transplantation Working Party Chronic Leukemia. Blood 1995; 86:2041-2050.

(3) Slavin S, Naparstek E, Nagler A, et al. Allogeneic cell therapy with donor peripheral blood cells and recombinant human interleukin-2 to treat leukemia relapse post allogeneic bone marrow transplantation. Blood. 1996;87(6):2195-2204.

(4) Perez P, Hoffman R W, Shaw S et al. Specific targeting of cytotoxic T cells by anti-T3 linked to anti-target cell antibody. Nature 1985; 316: 354-6.

(5) Segal D M, Sconocchia G, Titus J A et al. Alternative triggering molecules and single chain bispecific antibodies. J Hematother. 1995;4(5):377-82.

(6) Kudo T, Suzuki M, Katayose Y et al. Specific targeting immunotherapy of cancer with bispecific antibodies. Tohoku J Exp Med. 1999;188(4):275-88.

(7) Friedrich S W, Lin S C, Stoll B R et al. Antibody-directed effector cell therapy of tumors: analysis and optimization using a physiologically based pharmacokinetic model. Neoplasia. 2002;4(5):449-63.

(8) Baeuerle P A, Kufer P, Lutterbuse R. Bispecific antibodies for polyclonal T-cell engagement. Curr Opin Mol Ther. 2003;5(4):413-9.

(9) Lindhofer H, Mocikat R, Steipe B, et al.: Preferential species-restricted heavy/light chain pairing in rat/mouse quadromas. Implications for a single-step purification of bispecific antibodies. J Immunol 155: 219-25, 1995

(10) Lindhofer. H, Menzel H, Gunther W, Hultner L, Thierfelder S: Bispecific antibodies target operationally tumor-specific antigens in two leukemia relapse models. Blood 88:4651-8, 1996

(11) Renner C, Jung W, Sahin U et al: The role of lymphocyte subsets and adhesion molecules in T cell dependent cytotoxicity mediated by CD3 and CD28 bispecific monoclonal antibodies. Eur J Immunol 25:2027-33, 1995

(12) Dreier T, Lorenczewski G, Brandl C, Hoffmann P, Syring U, Hanakam F, Kufer P, Riethmüller G, Bargou R, Baeuerle P A: Extremely potent, rapid and costimulation-independent cytotoxic T cell response against lymphoma cells catalayzd by a single-chain bispeicifc antibody. Int J Cancer 100: 690-7, 2002

(13) Wimberger P, Xiang W, Mayr D, Diebold J, Dreier T, Baeuerle P A, Kimmig R. Efficient tumor cell lysis by autologous, tumor-resident T lymphocytes in primary ovarian cancer samples by an EP-CAM-/CD3-bispecific antibody. Int J Cancer. 2003 Jun 10;105(2):241-8.

(14) Kroesen B J, ter Haar A, Spakman H, Willemse P, Sleijfer D T, de Vries E G, Mulder N H, Berendsen H H, Limburg PC, The T H, Local antitumor treatment in carcinoma patients with bispecific-monoclonal-antibody-redirected T cells. Cancer Immunol Immunother 1993;37:400-7

(15) Canevari S, Stoter G, Arienti F, Bolis G, Colnaghi M I, Di Re E M, Eggermont A M, Goey S H, Gratama J W, Lamers C H. Regression of advanced ovarian carcinoma by intraperitoneal treatment with autologous T lymphocytes retargeted by a bispecific monoclonal antibody. J Natl Cancer Inst 1995;87:1463-9

(16) De Gast G C, Haagen I A, van Houten A A et al., CD8 T cell activation after intravenous administration of CD3× CD19 bispecific antibody in patients with non-Hodgkin lymphomas. Cancer Immunol Immunother 40:390-6, 1995

(17) Marme A, Strauss G, Bastert G, Grischke E M, Moldenhauer G:Intraperitoneal bispecific antibody (HEA 125× OKT3) therapy inhibits malignant ascites production in advanced ovarian carcinoma. Int J Cancer 101: 183-9, 2002

(18) Zeidler R, Mysliwietz J, Csanady M, Waltz A, Ziegler I, Schmitt B, Wollenberg B, Lindhofer H. The Fc-region of a new class of intact bispecific antibody mediates activation of accessory cells and NK cells and induces direct phagocytosis of tumor cells. British Journal of Cancer 2000;83(2):261-266.

(19) Riesenberg R, Buchner A, Pohla H et al. Lysis of prostate carcinoma cells by trifunctional bispecific antibodies (alpha EpCAM×alpha CD3). J Histochem Cytochem. 2001; 49(7):911-7

(20) Ruf P, Lindhofer H. Induction of a long-lasting anti-tumor immunity by a trifunctional bispecific antibody. Blood. 2001;98(8):2526-34.

(21) Slavin S. Immunotherapy of cancer with alloreactive lymphocytes. Lancet Oncology. 2001;2:491-498

(22) Childs R, Chemoff A, Contentin N et al. Regression of metastatic renal-cell carcinoma after nonmyeloablative allogeneic peripheral-blood stem cell transplantation. N Engl J Med. 2000;343(11):750-758.

(23) Slavin S, Morecki S, Weiss L et al. Immunotherapy of hematologic malignancies and metastatic solid tumors in experimental animals and man. Critical Reviews in Oncology/Hematology 2003;46:139-163.

(24) Sullivan K M, Weiden P L, Storb et al. Influence of acute and chronic graft-versus-host disease on relapse and survival after bone marrow transplantation from HLA-identical siblings as treatment of acute and chronic leukemia. Blood. 1989;73(6):1720-8.

(25) Cohen P, Vourka-Karussis U, Weiss L et al. Spontaneous and IL-2 induced anti-leukemic and anti-host effects against tumor- and host-specific alloantigens. J Immunol. 1993;151:4803-4810.

(26) Morecki S, Yacovlev E, Diab A et al. Allogeneic cell therapy for a murine mammary carcinoma. Cancer Res. 1998; 58:3891-3895.

(27) Morecki S, Yacovlev E, Gelfand Y, Uzi I, Slavin S. Cell therapy with preimmunized effector cells mismatched for minor histocompatible antigens in the treatment of a murine mammary carcinoma. J Immunother. 2001 24(2): 114-21.

(28) Slavin S. Cancer Immunotherapy with alloreactive lymphocytes. N Engl J Med. 2000;343 :802-803.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method of substantially reducing or avoiding a graft versus host disease during treatment of tumor growth and metastasis in a mammal, said method comprising in vivo administering allogeneic effector cells together with trifunctional bispecific antibodies having the following properties:
   a) binding to CD3 on a T cell
   b) binding to at least one antigen on a tumor cell
   c) binding via their Fc portion to Fc receptor positive cells,
   d) having one of the following subclass combinations:
      i) rat-IgG2b/mouse-IgG2a,
      ii) rat-IgG2b/mouse-IgG2b,
      iii) rat-IgG2b/human-IgG1,
      iv) mouse-[VH-CH1, VL-CL]-human-IgGI/rat-[VH-CH1, VL-CL]-human-IgG1[hinge]-human-IgG3*-[CH2-CH3] wherein*=caucasian allotypes G3m(b+g)=no binding to protein A,
   wherein said allogeneic effector cells are Fc receptor positive cells and are a combination of lymphoid cells comprising T cells, NK cells and B cells and myeloid cells comprising monocytes and optionally additionally macrophages or dendritic cells or a combination thereof, whereby said tumor growth and metastasis is treated and graft versus host disease is substantially reduced or avoided in said mammal.

2. A method of treating tumor growth and metastasis in a mammal according to claim 1, wherein said allogeneic effector cells are lymphoid or myeloid cells or a combination thereof used in the form of peripheral blood mononuclear cells, whole bone marrow cells, cord blood and splenic cells.

3. A method of treating tumor growth and metastasis in a mammal according to claim 1, wherein said allogeneic effector cells are derived from a donor, matched or mismatched in HLA type to the host.

4. A method of treating tumor growth and metastasis in a mammal according to claim 1, wherein before administering said allogeneic effector cells together with said antibodies said mammal is treated in order to reduce its tumor load.

5. A method of treating tumor growth and metastasis in a mammal according to claim 1, wherein said mammal had not received an allogeneic hematopoietic stem cell or allogeneic bone marrow transplantation and wherein before administering said allogeneic effector cells together with said antibodies said mammal is treated in order to induce a mild immunosuppression or conditioning to allow said administered allogeneic effector cells to survive for a time period which is necessary to accomplish tumor cell killing by said antibodies before a rejection reaction against said effector cells is initiated.

6. A method of treating tumor growth and metastasis in a mammal according to claim 5 wherein said treatment to induce a mild immunosuppression or conditioning is performed by irradiation.

7. A method of treating tumor growth and metastasis in a mammal according to claim 1, wherein before administering said allogeneic effector cells together with said antibodies said mammal had undergone hematopoietic stem cell transplantation or bone marrow transplantation.

8. A method of treating tumor growth and metastasis in a mammal according to claim 1, wherein before administering said allogeneic effector cells together with said antibodies said mammal is treated in order to reduce its tumor load by irradiation, chemotherapy, immune therapy, surgery or a combination thereof.

9. A method of treating tumor growth and metastasis in a mammal according to claim 1, wherein said trifunctional antibodies are heterologous rat/mouse bi-specific antibodies.

10. A method of treating tumor growth and metastasis in a mammal according to claim 1, wherein said trifunctional antibodies are mouse IgG2a/rat IgG2b heterologous bi-specific antibodies.

11. A method of treating tumor growth and metastasis in a mammal according to claim 1, wherein said at least one antigen on a tumor cell recognized by said trifunctional antibodies is one of EpCAM, Her2/neu, EGF-receptor, GD2, GD3, G250, CEA, CD20, CD22, CD30, CD33, CD38 or CD138.

12. A method of treating tumor growth and metastasis in a mammal according to claim 1, wherein said tumor is a malignant tumor selected from leukemia, malignant lymphoma chronic myelogenous leukemia (CML). acute leukemia, chronic lymphocytic leukemia (CLL), myelodysplasia (MDS), Hodgkin disease, non-Hodgkin lymphoma (NHL), multiple myeloma, sarcoma, melanoma, brain tumor, stomach cancer, tongue cancer, esophageal carcinoma, colorectal cancer, liver cancer, gallbladder carcinoma, pancreatic carcinoma, renal carcinoma, bladder cancer, nasopharyngeal cancer, laryngeal cancer, skin cancer, mammary cancer, testicular cancer, ovarian cancer, uterus carcinoma, and lung cancer.

13. A method of treating tumor growth and metastasis in a mammal according to claim 1, wherein said antibodies are used in an amount of 10-100 µg/patient and treatment.

14. A method of treating tumor growth and metastasis in a mammal according to claim 1, wherein said mammal is a human.

15. A method of treating tumor growth and metastasis in a mammal according to claim 1, wherein said binding to Fc receptor positive cells comprises binding to Fcγ receptor type I or Fcγ receptor type III.

* * * * *